(12) United States Patent
Nihei et al.

(10) Patent No.: US 6,296,484 B1
(45) Date of Patent: Oct. 2, 2001

(54) DISPENSER FOR DENTAL VISCOUS MATERIAL

(75) Inventors: Tsutomu Nihei, Tokyo; Kazuya Ishida, Minaminasu-Machi, both of (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/550,594

(22) Filed: Apr. 17, 2000

(30) Foreign Application Priority Data

Apr. 28, 1999 (JP) .................................................. 11-122259

(51) Int. Cl.[7] ....................................................... A61C 5/04
(52) U.S. Cl. ............................................. 433/89; 222/391
(58) Field of Search ....................... 433/89, 90; 222/391, 222/386

(56) References Cited

U.S. PATENT DOCUMENTS

| | | | | |
|---|---|---|---|---|
| 1,871,399 | * | 8/1932 | Adams | 222/391 |
| 5,263,614 | * | 11/1993 | Jacobsen et al. | 222/391 |
| 5,823,403 | * | 10/1998 | Schneider | 222/391 |
| 5,871,354 | * | 2/1999 | Kunkel et al. | 433/90 |

* cited by examiner

Primary Examiner—John J. Wilson
(74) Attorney, Agent, or Firm—Oblon, Spivak, McClelland, Maier & Neustadt, P.C.

(57) ABSTRACT

A dispenser for dental viscous material including a box-shaped handle provided with a cartridge-mounting portion for mounting a cartridge containing a dental viscous material. A guide shaft is supported in the front and back direction in a cavity of the box-shaped handle, at a preset position of which is provided a lever-engaging portion. A lever is provided in the box-shaped handle via a lever shaft, one end of which is engaged with the lever-engaging portion of the guide shaft and the other end of which is positioned outside the box-shaped handle. An elastic member is engaged with the box-shaped handle and the guide shaft or the lever so as to return the guide shaft to an initial position.

5 Claims, 2 Drawing Sheets

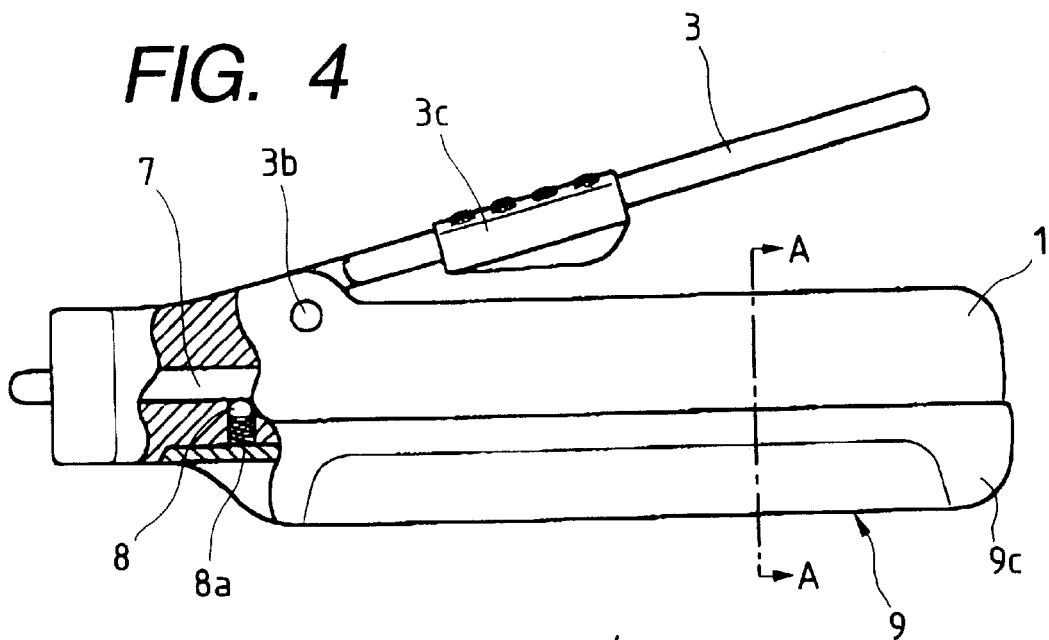
FIG. 4
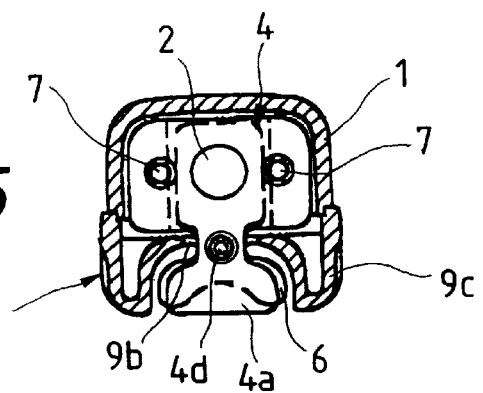
FIG. 5
FIG. 6
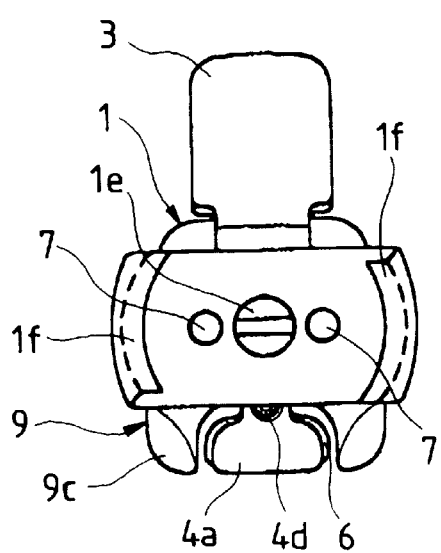
FIG. 7
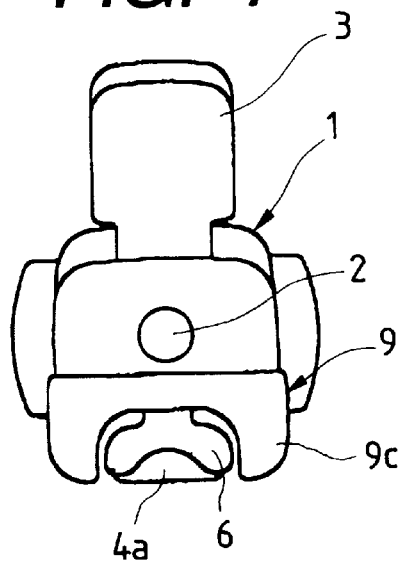

DISPENSER FOR DENTAL VISCOUS MATERIAL

BACKGROUND OF THE INVENTION

1. Field of the Invention

The present invention relates to a dispenser for dental viscous material which is not only cable of discharging a desired amount of a dental viscous material contained in a cartridge but also free from a "after flow" phenomenon in which even after the discharge operation has been stopped, the dental viscous material is continued to be discharged out due to a residual pressure in the cartridge (the dispenser for dental viscous material will be sometimes simply referred to as "dispenser" in some cases).

2. Description of the Conventional Art

Dental viscous materials to be used in a field of the dental treatment are commercially available depending upon an object of use thereof, including impression material, filling material, and adhering material (the dental viscous material will be sometimes simply referred to as "viscous material"). Some typical examples of the use thereof are explained below.

For example, in case where a viscous material is formed by a combination of two or more kinds of materials, just before the use, necessary amounts of the materials are taken out from the respective containers (in almost all cases, the materials are weighted and used in equivalent amounts or in equal lengths) and placed on a mixing pad, etc., which are then mixed with each other and put into use. Also, there are an example in which a powder and a liquid, each of which has been previously weighted in a capsule, are mixed with each other to form a paste (in a viscous state), which is then put into use; and an example in which a viscous material as previously contained in a container is directly filled into a dental cavity for which the preparation in an oral cavity has been made, from the container (the container will be sometimes simply referred to as "cartridge).

In the case where the viscous materials are weighted and put into use, tubes are generally used for the containers, and a mixing pad on which a scale mark for measuring the length has been previously printed is used. And, in case where it is required that the amounts of the respective viscous materials are different, there is a measure that apertures of the tube outlets are different while the lengths are equal. Operators, such as dentists and dental hygienists, mixed these materials on a mixing pad and put them into use. At this time, since they must take care that air bubbles or the like are not entrained, while paying attention that these materials are thoroughly mixed, the mixing works relatively required skill and were annoying.

As instruments that are provided for the purpose of liberating the operators from the works that require skill and are annoying, there are devices (applicators) as disclosed in Japanese Patent Publication No. 55195/1993, Japanese Patent Publication No. 30762/1995 and International Patent Publication No. 502464/1999. In these applicators, one or two cartridges containing the viscous material are installed in a device having a pistol-like shape for use. A discharge outlet of the cartridge is installed with a mixing tool as disclosed in Japanese Patent Publication No. 8290/1969 (the mixing tool will be sometimes referred to as "nozzle"). By using such a nozzle, the material to be discharged from the opening at a tip of the nozzle is thoroughly mixed during the step of passing through the nozzle and is in a state that it can be immediately put into use. At this time, as a driving source of this device is used a human power or compressed air.

In addition, examples of devices for discharging the viscous material as the contents from the capsule or cartridge include devices as disclosed, for example, in Japanese Patent Laid-Open No. 276550/1986, Japanese Patent Laid-Open No. 253095/1997, and Japanese Patent Laid-Open No. 43206/1998. These devices mainly have an appearance like a pistol and are arranged with an installation portion (e.g., a concave of the connector portion) for installing the capsule or cartridge in a predetermined position at the front of the device. And, any of these devices are provided with a piston rod for pressing and extruding the viscous material in the capsule or cartridge. As a driving source for advancing the piston rod to the extrusion direction of the viscous material, a human power is used in any of the cases.

In various devices as described above, as to those in which a human power is used as the driving source are roughly classified into the following two groups according to the mechanism for advancing the piston rod in the extrusion direction of the viscous material.

One of the two groups is of a ratchet mechanism type for obtaining advancing and braking (stopping) effects by a combination of a rack and a claw; and the other is of a jamming mechanism type for obtaining advancing and braking (stopping) effects by inclining a plate bored with a hole through which the piston rod is to be penetrated and which has a size slightly larger than that of an outer diameter of the piston rod, against the axis of the piston rod and bringing the piston rod into contact with an edge of the hole.

Examples of the former ratchet mechanism type include devices as disclosed in Japanese Patent Publication No. 55195/1993 and International Patent Publication No. 502464/1999. Also, examples of the latter jamming mechanism type include devices (applicators) as disclosed in Japanese Patent Laid-Open No. 276550/1986 and Japanese Patent Laid-Open No. 43206/1998. The both mechanisms have merits and demerits, respectively.

First of all, the outline of the mechanism of the ratchet mechanism type is explained. What the piston rod is advanced in the extrusion direction of the viscous material is effected by an engagement of a row of rack formed on the piston rod with a claw. And, to impart a movement to the claw is effected by a human power through handle operation (in some cases, a motor is used). The ratchet mechanism type has the following merits. That is, the piston rod can be surely advanced in a constant distance by a single handle operation (hence, the measurement of the material to be discharged is accurate); and a cartridge containing a relatively highly viscous material can also be used. Further, from the mechanical viewpoint, restrictions in designing is decreased, so that a relatively thin piston rod can be used, leading to realizing decrease in size.

On the other hand, the ratchet mechanism type involves the following demerits. That is, from the operational viewpoint, the piston rod must be advanced in the extrusion direction after blank shots of the handle until the material in the cartridge has reached a certain position (a position of an inner lid functioning to press the material in the cartridge); measurement of the material to be discharged at a first handle operation is inaccurate (due to the fact that at the first handle operation, a tip of the piston rod cannot be brought into contact with a rear portion of the inner lid functioning to press the material in the cartridge to cause the material to be throw away, and such is wasteful); the movement of the piston rod is restricted by the size or position of the rack; and even after the handle operation has been stopped, the material is discharged due to the residual pressure in the cartridge (such phenomenon is called as "afterflow"). Also, from the processing viewpoint, a relatively high processing precision is required (leading to high costs); and when a safety is taken into consideration, the mechanism inevitably becomes complicated, thereby increasing the number of component members.

Next, the outline of the mechanism of the jamming mechanism type is explained. The movement in the extrusion direction and braking (stopping) of the piston rod are effected by inclining at least one of two plates bored with a hole through which the piston rod is to be penetrated and which has a size slightly larger than that of an outer diameter of the piston rod, against the axis of the piston rod (in order to impart a force to the inclined plate, an elastic member such as a coil spring is generally used) and bringing the piston rod into contact with an edge of the hole. And, by using a lever or the like while utilizing the principles of the lever, the previously inclined plate is aligned perpendicular to the axis of the piston rod (namely, in a state that it does not hinder the movement of the piston rod resisting to the force of the elastic member imparted to the plate), thereby moving (advancing) the piston rod in the extrusion direction while utilizing a contact resistance (friction) of the edge of the hole of the previously inclined plate.

The jamming mechanism type has the following merits. That is, from the operational viewpoint, since the piston rod can be advanced in the beginning to an arbitrary position (free from the restrictions as in the row of rack), a tip of the piston rod can be moved to a position at which it comes into contact with a rear portion of an inner lid functioning to press the material in the cartridge, so that blank shots of the handle are not required, and the material to be first discharged can be used as a material that has been properly measured; and the afterflow phenomenon is substantially not caused. From the mechanical viewpoint, the construction is simple; and since the precision is not required as compared with the ratchet mechanism type, it is inexpensive.

On the other hand, as demerits, there are cases where the above-described merits will bring about a backfired result. That is, from the operational viewpoint, when an inner pressure of the material in the cartridge increases, the advancing of the piston rod is hindered (since the advancing of the piston rod relies upon a friction force between the plate and the piston rod, when the friction force does not overcome the inner pressure of the material in the cartridge, it is impossible to ensure advancing at a constant stroke), and therefore, the measurement becomes inaccurate; and a highly viscous material cannot be applied. From the mechanical viewpoint, since it is difficult to ensure the strength, the miniaturization cannot be realized; and it is not avoidable that the piston rod is backed during a loss time at the moment when the two plates are returned to the original positions (due to a reaction force of the material in the cartridge).

In the light of the above, it can be understood that both of the ratchet mechanism type and the jamming mechanism type have noteworthy merits and that these merits are existent so as to compensate the respective demerits. However the ratchet mechanism type is, if anything, more reliable in behavior and is greater in a degree of freedom for the design than the jamming mechanism type, and hence, the former is mainly used. This is also understood from a fact that an applicator as disclosed in International Patent Publication No. 502464/1999 is designed so as to prevent a container from breakage due to a high pressure, thereby improving the above-described demerits.

In addition, in the description regarding the explanation of an applicator as disclosed in Japanese Patent Laid-Open No. 43206/1998 relating to the jamming mechanism type device, there are found the following descriptions: in section No. 0050, "According to a further especially advantageous embodiment it is suggested to provide the piston rod 16 in the engagement area of the actuator jamming element 30 with a micro toothing." and in section No. 0051, "It may be easier to provide the entire piston rod 16 with the micro toothing." In short, it may be considered that such is a measure for more ensuring the advancing the piston rod. Hence, according to the description of this patent publication, it can also be said that such description refers to a fact that only the construction of the jamming mechanism type is not at all times sufficient for achieving the advancing of the piston rod.

SUMMARY OF THE INVENTION

The present invention is aimed to provide a dispenser for dental viscous material that have the merits of both of the ratchet mechanism type and the jamming mechanism type as described above but is free from the demerits.

Specifically, an object of the present invention is to provide a dispenser that can surely press a material contained in a cartridge at a constant stroke, while it is of a construction of the jamming mechanism which can discharge the material with an accurate measurement from the first discharge, nonetheless various materials from low-viscosity materials to high-viscosity materials can be applied and which is free from a afterflow phenomenon.

In order to achieve the above-described object, we, the present inventors made extensive and intensive investigations. As a result, it has been found that this object can be attained by a dispenser for dental viscous material having a structure, comprising a box at a front end of which is provided a cartridge-mounting portion for mounting a cartridge containing a dental viscous material; a guide shaft supported slidably in the front and back direction in a cavity of the box, at a predetermined position of which is provided a lever-engaging portion; a lever mounted oscillatorily in the box via a lever shaft, one end of which is engaged with the lever-engaging portion of the guide shaft and the other end of which is positioned outside the box; an elastic member engaged with the box and the guide shaft or the lever so as to return the guide shaft to an initial position; a slide block having therein a space whose lower side is opened and having a box-like outer shape corresponding to a shape of the cavity of the box and being screwed with an adjusting screw at a position lower than a through hole bored in a front side wall member, through which is penetrated the guide shaft in the front and back direction; a pressing spring for pressing forward a release plate bored with a hole having a size slightly larger than that of the guide shaft and having a shape corresponding to that of the guide shaft, through which is penetrated the guide shaft, the release plate being able to be mounted so as to be inclined against an axis of the guide shaft by adjusting a backward protruded length of the adjusting screw, and the pressing spring being aligned between a rear side wall member of the slide block and the release plate; a piston shaft for pressing the viscous material in the cartridge from the rear side, the piston shaft having an axis in parallel to that of the guide shaft and being fixed to the slide block; and a braking member for at all times pressing the piston shaft by an elastic force of a braking elastic member, the braking member being aligned in the box.

And, in the above-described structure, it has also be found that:

when the braking member is spherical, and the braking elastic member for at all times pressing the braking member against the piston shaft is a coil spring, the structure is simple and durable;

when the elastic member for returning the guide shaft to an initial position is a coil spring whose one end face comes into contact with a front end face of the guide shaft and whose another end face comes into contact with an end face of a set screw to be screwed with a female screw provided in a first half portion of a front mounting hole of the box, the screwing position of the set screw being movable in the front and back direction, it is easy to not only return the guide shaft to the initial position but also change a stroke of the guide shaft;

when a back lid is fixed in a lower side of the box, and the back lid is provided with a skirt portion, which is deeper than the front side wall member of the slide block protruding from a bottom face of the box and a lower end of the release plate, it is convenient to place the dispenser for dental viscous material horizontally; and when a stopper having a portion protruding downward is mounted movably in an intermediate portion of the lever, an oscillatory angle of the lever can be freely set up, and the stroke of the guide shaft can be changed.

BRIEF DESCRIPTION OF THE DRAWINGS

FIG. 4 is a view to show a front elevation of a partial cross section of a front portion of the dispenser for dental viscous material as shown in FIG. 1;

FIG. 5 is an explanatory view to show an A—A line cross section of FIG. 4;

FIG. 6 is a view to show a left side of the dispenser for dental viscous material as shown in FIG. 1; and FIG. 7 is a view to show a right side of the dispenser for dental viscous material as shown in FIG. 1.

DESCRIPTION OF THE PREFERRED EMBODIMENTS

Now, the dispenser for dental viscous material according to this invention is explained in detail with reference to the accompanying drawing.

Figure 1:
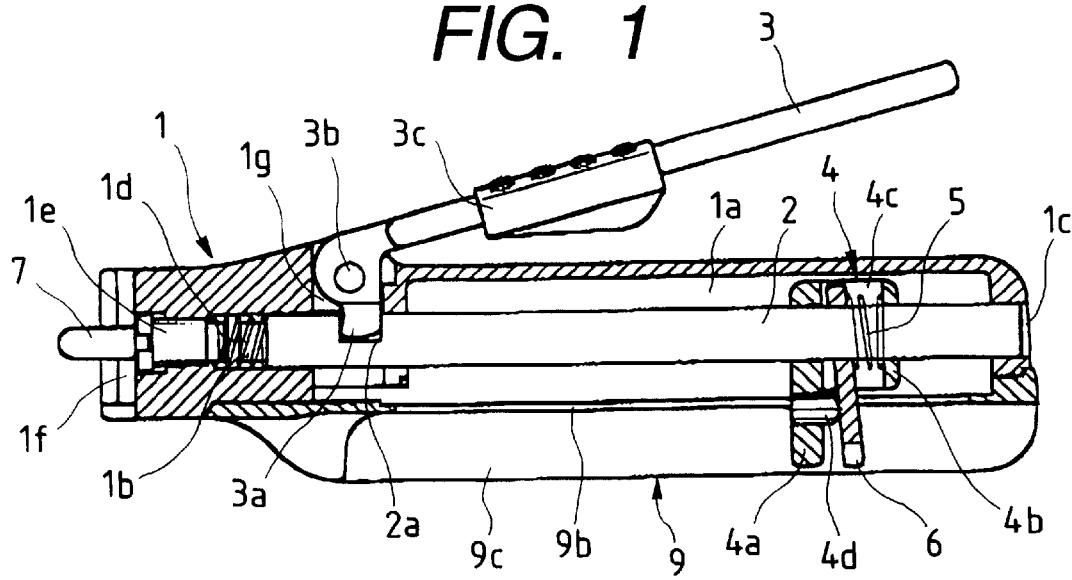
FIG. 1 is an explanatory view to show a longitudinal section of a center of a box in one embodiment of a dispenser for dental viscous material according to the present invention.
Figure 2:
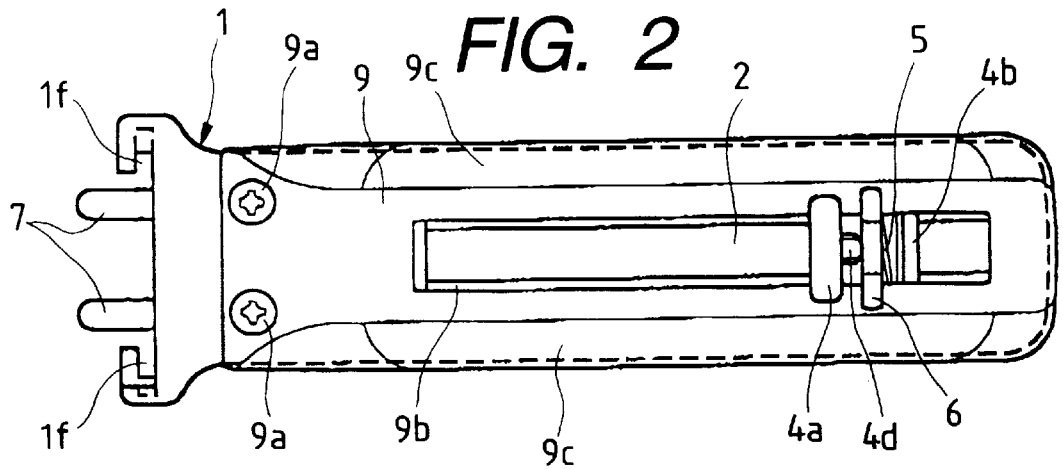
FIG. 2 is a view to show a bottom of the dispenser for dental viscous material as shown in FIG. 1.
Figure 3:
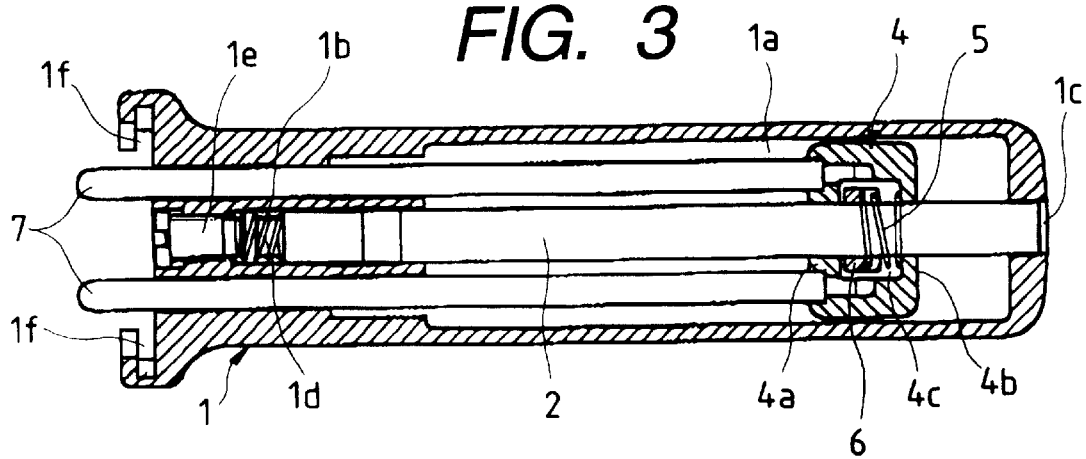
FIG. 3 is an explanatory view to show a cross section of the center of the box of the dispenser for dental viscous material as shown in FIG. 1.

FIG. 1 is an explanatory drawing to show a longitudinal section of a center of a box in one embodiment of a dispenser for dental viscous material according to this invention; FIG. 2 is a drawing to show a bottom of the dispenser for dental viscous material as shown in FIG. 1; FIG. 3 is an explanatory drawing to show a traverse cross section of the center of the box of the dispenser for dental viscous material as shown in FIG. 1; FIG. 4 is a drawing to show a front elevation of a partial cross section of a front portion of the dispenser for dental viscous material as shown in FIG. 1; FIG. 5 is an explanatory drawing to show an A—A line cross section of FIG. 4; FIG. 6 is a drawing to show a left side of the dispenser for dental viscous material as shown in FIG. 1; and FIG. 7 is a drawing to show a right side of the dispenser for dental viscous material as shown in FIG. 1.

In the drawings, a numeral 1 shows a box in an approximately square pole shape, which is preferably made of a light-weight material with a superior strength, such as light metals, e.g., aluminum alloys or engineering plastics, and at a front end of which is provided cartridge-mounting portion 1f for mounting a cartridge containing a dental viscous material. In an interior of the box 1 is provided a cavity 1a, a lower side of which is opened, and a lever-mounting hole 1g connecting to the cavity 1a is bored at a predetermined position of a front portion of an upper side of the box 1. Also, consideration is taken such that a portion for forming front and rear walls to form the cavity 1a has a sufficient thickness as compared with other portions. This is to support a guide shaft 2 as described later so that the guide shaft may move slidably. Front and rear walls of the box 1 are bored with a front mounting hole 1b and a rear mounting hole 1c so as to have a common single axis. Needless to say, these mounting holes 1b, 1c have a shape corresponding to that of a longitudinal section of the guide shaft 2, but in order that the guide shaft 2 can easily slide in the front and back direction, a bearing may be aligned.

A numeral 2 denotes a rod-like guide shaft made of a metallic material such as stainless steel. While it is desired that the guide shaft 2 is shaped in a round bar state because the processing cost is inexpensive, even when it is shaped to have a polygonal or elliptic cross section, there are no particular problems in its object and function. As described previously, the guide shaft 2 is mounted such that it is inserted into each of the front mounting hole 1b and rear mounting hole 1c of the box 1 in a bridging state. On an upper side at a predetermined position of a front portion (a left side in FIG. 1) of the guide shaft 2 is aligned a lever-engaging portion 2a (a groove-like engaging concave in the embodiment shown in the drawings), which is coincident with the position of the lever-mounting hole 1g bored in the upper side of the box 1.

A numeral 3 is a lever having a plate-like shape, etc., mounted oscillatorily in the vertical direction in the box 1 via a lever shaft 3b aligned in an aperture of the lever-mounting hole 1g in the upper side of the box 1, in which in one end of the lever 3, a guide shaft-engaging portion 3a (an engaging protrusion in the embodiment shown in the drawings) is engaged with the lever-engaging portion 2a of the guide shaft 2, and the other end is positioned outside the box 1. It is preferred that the lever 3 has a breadth slightly smaller than the breadth of the box 1 as shown in FIGS. 6 and 7.

By this structure, the oscillation of the lever 3 is a lever-movement with the lever shaft 3b as a fulcrum, and thus, the guide shaft 2 slides in the front and back direction coincident with the movement of the lever 3. Needless to say, so far as the above-described movement is obtained in the relation between the guide shaft 2 and the lever 3, an embodiment in which the alignment between the engaging concave as the lever-engaging portion 2a of the guide shaft 2 and the engaging protrusion as the guide shaft-engaging portion 3a of the lever 3 is reversed, and an embodiment in which the respective protrusions as aligned are connected to each other by means of pins, etc. also fall within the scope of the present invention. In addition to the assurance of the movement, the above-described structure also contributes to prevention of the guide shaft 2 from dropping from the box 1.

On the other hand, an operator moves the lever 3, and the lever 3 is returned to an initial position while utilizing an elastic force of an elastic member 1d. The alignment of the elastic member 1d includes various embodiments wherein the elastic member 1d is engaged with the box 1 and the guide shaft 2 or the lever 3. For instance, as in the embodiment as shown in the drawings, there is an embodiment in which a coil spring as the elastic member 1d is engaged with the box 1 and the guide shaft 2 such that in an interior of the front mounting hole 1b of the box 1, one end face of the coil spring comes into contact with a front end face of the guide shaft 2, and that the other end face comes into contact with an end face of a set screw 1e to be screwed with a female screw provided in a first half portion of the front mounting hole 1b of the box 1, the screwing position of the set screw 1e being movable in the front and back direction.

In the case of this embodiment, when an end portion of the lever 3 is pushed down in the side of the box 1, the guide shaft 2 moves forward via the lever-engaging portion 2a of the guide shaft 2, with which the guide shaft-engaging portion 3a of the lever 3 is engaged, thereby pressing the coil spring as the elastic member 1d. And, when a force applied to the lever 3 is released, a pressing force that has been applied to the elastic member 1d is also released. Therefore, the guide shaft 2 is returned to the initial position due to its elastic force, and the lever 3 is also returned to the initial position coincidentally.

Further, by adjusting a protruding length of the set screw 1e in the side of the guide shaft 2, it becomes possible to adjust a force for pushing down the lever 3 in the side of the box 1, or a stroke (traveling distance) of the guide shaft 2 in the front and back direction. This is because when the set screw 1e is protruded on the side of the guide shaft 2, the coil spring as the elastic member 1d shrinks, whereby an initial force to be applied to the guide shaft 2 becomes large; and the coil spring as the elastic member 1d becomes in a tight state, whereby the guide shaft 2 can no longer travel in the side of the set screw 1e.

In the above-described embodiment, the elastic member 1d is a compression coil spring provided in the front mounting hole 1b on the side of the front end face of the guide shaft 2, but it may be provided in the side of a rear end face of the guide shaft 2. In this case, since a tensile coil spring is used, there may be used a structure in which the guide shaft 2 is tensed backward (for instance, a structure in which protrusions are provided in the guide shaft 2 and the cavity 1a in the interior of the box 1 and hooked with a tensile coil spring).

In these embodiments, when a stopper 3c having a portion protruding downward is mounted movably in an intermediate portion of the lever 3, a lower end of the stopper 3c comes into collision with an upper face of the box 1, whereby the lever 3 oscillates only at a constant angle, namely, when the lever 3 is rotated only with a desired angle, the stopper 3c comes into collision with an upper face of the box 1, whereby the lever 3 cannot be rotated downward. Thus, the stroke of the guide shaft 2 can be controlled. And, needless to say, in order to adjust the stroke of the guide shaft 2, the above-described set screw 1e and stopper 3c can be used alone or in combination.

Besides, a structure in which the elastic member 1d is aligned for the structure in which the lever 3 is at all times is pressed may be used. This embodiment corresponds to an embodiment in which one or two torsion coil springs are aligned at a position of the lever shaft 3b, thereby at all times pushing upward the lever 3 against the box 1, and are engaged with the box 1and the lever 3. In the light of the above, in the structure of the dispenser for dental viscous material according to the present invention, it is possible to mount and align various types of the elastic material 1d. In other words, the invention takes any structure so far as a force is applied such that the guide shaft 2 and the lever 3 are returned to the original positions, respectively.

A numeral 4 shows a slide block having therein a space 4c whose lower side is opened and having a box-like outer shape corresponding to a shape of the cavity 1a. Each of a front side wall member 4a and a rear side wall member 4b as wall members of the slide block 4 in the front and back direction is bored with a through hole, through which is penetrated the guide shaft 2, corresponding to the shape of the traverse cross section of the guide shaft 2. And, a female screw is screwed at a position lower than the through hole of the front side wall member 4a for the guide shaft 2, and this female screw is screwed with an adjusting screw 4d.

In the space 4c of the slide block 4, a pressing spring 5 and a release plate 6 are aligned, that are penetrated therethrough with the guide shaft 2. In the relation between the both, the pressing spring 5 is aligned between the rear side wall member 4b and the release plate 6. By using such construction wherein a compression coil spring as in the embodiment shown in the drawings and a leaf spring are used as the pressing springs 5, the release plate 6 is at all times applied with a force to be applied backward.

And, the hole bored in the release plate 6 has a shape slightly larger than the thickness of the guide shaft 2 and corresponding to the shape of the guide shaft 2. Also, since a tip of the adjusting screw 4d screwed in the female screw screwed at a position lower than the through hole of the front side wall member 4a of the slide block 4 for the guide shaft 2 is protruded on the side of the rear side wall member 4b, an upper side of the release plate 6 is pushed forward by the pressing coil spring 5, whereas a lower side of the release plate 6 is prevented from traveling forward by the adjusting screw 4d.

Accordingly, so the hole bored in the release plate 6 is slightly larger than the thickness of the guide shaft 2 and has a clearance with the guide shaft 2. Therefore, in a usual state, the release plate 6 is inclined against an axis of the guide shaft 2 as shown in FIG. 1. And, when the release plate 6 is inclined in this manner, an edge of the hole bored in the release plate 6 comes into contact with the guide shaft 2, and a friction force plays a role as a brake with the guide shaft 2. As a result, it becomes possible that the whole of the slide block 4 keeps its position (namely, is fixed) at an arbitrary position on the shaft guide 2.

As shown in FIGS. 3 and 5, rear ends of two piston shafts, 7, 7, each having an axis in parallel the guide shaft 2, are each fixed to the slide block 4, thereby pressing the viscous material in the cartridge from the rear side. As a result, the two piston shafts 7, 7 are integrated with the slide block 4 to undergo the traveling in the front and back direction. In other words, the piston shaft 7 slides and moves in the through holes for the piston shaft 7, which are previously bored in the wall on the front side of the box 1 in correspondence with the number of the piston shaft to be used, and protrudes outside the box 1 or is accommodated inside of the box 1. The number of the piston shafts 7 to be used is properly set up within a range of from 1 to 4 (two piston shafts in the embodiment as shown in the drawings) corresponding to the number of a cartridge(s) (not shown in the drawings) containing the dental viscous material to be mounted. And, the piston shaft 7 may be made exchangeable so as to select the length of the piston shaft 7 coincident with the cartridge to be used. For this purpose, it is preferred to provide a structure in which the fixation of the rear end of the piston shaft 7 to the slide block 4 is effected by screwing a male screw screwed in the rear end of the piston shaft 7 into a female screw screwed in the slide block 4.

A numeral 8 is a braking member aligned in a lateral hole connecting to the hole for piston shaft 7, which is penetrated and bored in the front side wall member of the box 1, and is at all times pressed against the piston shaft 7 penetrating through the hole for the piston shaft 7 by a compression coil spring as a braking elastic member 8a to be aligned in a lower portion thereof. As a result, the piston shaft 7 is in a state that it is hard to move in the front and back directions.

The compression coil spring as the braking elastic member 8a is kept such that it remains in the lateral hole by a back lid 9 that is fixed on a lower side of the box 1 by a back lid-stopping screw 9a, as shown in FIG. 2. And, the braking member 8 is preferably spherical so that it does not limit the movement of the piston shaft 7 more than it needs. Further, when taking into consideration the wear, the braking member 8 is preferably made of a rigid material such as stainless steel.

The back lid 9 is provided with a skirt portion 9c, which is deeper than the front side wall member 4a of the slide block 4 protruding from a bottom face of the box 1 and a lower end of the release plate 6. This is because when the skirt portion 9c is present, even if the front side wall member 4a of the slide block 4 and the release plate 6 protrude from the bottom face of the box 1, it is possible to place the dispenser for dental viscous material according to the present invention horizontally, while separating the bottom face of the box 1 from a surface of a material on which the dispenser for dental viscous material according to this invention is placed (for instance, a flat face of a tray or cart of dental unit). This is a merit for an operator to easily grip the front side wall member 4a of the slide block 4 and the release plate 6 by fingers. Also, the interior of the box 1 may be protected by boring a guide hole 9b in the back lid 9 so as to limit the length of the movement of the slide block 4 in the front and back direction.

Next, how to use the dispenser for dental viscous material according to this invention in the embodiment as shown in the drawings is explained below.

First, it is confirmed that the piston shaft 7 is completely accommodated in the box 1. And, a center of the rear end of each of dual cartridges (not shown), each of which contains a different dental viscous material from each other, is brought into contact with the front end face of the box 1, while paying attention such that it is made substantially coincident with the center of the set screw 1e screwed with the box 1. At this time, a flange aligned in the rear end of the cartridge is made slightly hang on the groove of the cartridge-mounting portion 1f. Thereafter, by rotating the cartridge, the flange is screwed into the groove of the cartridge-mounting portion 1f. Thus, the mounting of the cartridge in the disperser is completed.

After the amounting of the cartridge has been completed, when a force is applied so as to push the release plate 6 in the slide block 4 protruding in the lower portion of the box 1 by fingers, the release plate 6 becomes substantially perpendicular against the guide shaft 2. Therefore, the brake is released, whereby the whole of the slide block 4 can freely move on the guide shaft 2 in the front and back direction. Then, the slide block 4 is moved forward until the tip of the piston shaft 7 has come into contact with the inner lid in the cartridge (the inner lid plays a role to set the dental viscous material to be contained apart from the outside). Whether or not the tip of the piston shaft 7 has come into contact with the inner lid can be readily felt in by an impact that the fingers receive.

After such preparation has been completed, the lever 3 is pushed down while revolving it around the lever shaft 3b as much as possible towards the side of box 1. Thus, the guide shaft 2 travels forward only at a previously determined stroke via the lever-engaging portion 2a, with which is engaged the guide shaft-engaging portion 3a positioned in a lower portion than the lever shaft 3b of the lever 3. During this time, since the release plate 6 present in the space 4c of the slide block 4 is inclined, a large friction force acts on between an edge of the through hole and the guide shaft 2. As a result, the slide block 4, the pressing spring 5, the release plate 6 and the piston shaft 7 are integrated and travel forward at a rate corresponding to the above-described stroke, and the inner lid in the cartridge is moved forward by the piston shaft 7, whereby the dental viscous material is discharged from the nozzle at the tip of the cartridge.

Thereafter, when the pushing-down force to the lever 3 is released, the guide shaft 2 is returned backward (i.e., returned to the original position) by the function of the elastic member 1d. At this time, while the friction is slightly present between the guide shaft 2 and the release plate 6, they are in a free state (since the release plate 6 is inclined forward as shown in FIG. 1, when the guide shaft 2 travels backward, the release plate 6 stands up). Accordingly, though the piston shaft 7 tries to return backward, the force received from the brake member 8 is so strong that the piston shaft 7 retains at this position without going down. By repeating such operations. The dental viscous material in the cartridge is discharged by constant amount.

In such operations, it is a well-known fact that when the shell diameter of the cartridge or the aperture of the nozzle is small, the inner pressure of the dental viscous material in the cartridge becomes considerably high. As described above, this causes the "afterflow" phenomenon after stopping the operations. However, in the dispenser for dental viscous material according to the present invention, since the movement of the piston shaft 7 is controlled by the friction force by the braking member 8 (this friction force being proportionate to the spring force of the braking elastic member 8a), in case that the inner pressure of the dental viscous material in the cartridge increases over a certain force, the piston shaft 7 is automatically pushed down backward, and the pressure is released. At this time, if the spring force of the braking elastic member 8a is selected depending upon the viscosity of the dental viscous material contained in the cartridge, the convenience for use is improved, and hence, such is preferable.

As described above in detail, the dispenser for dental viscous material according to this invention is a superior dispenser for dental viscous material having merits of both of a ratchet mechanism type and a jamming mechanism type. That is, in accordance with the dispenser for dental viscous material according to the present invention, not only the piston shaft can be surely advanced as in the ratchet mechanism type, but also after advancing the piston shaft until the tip of the piston shaft has come into contact with the inner lid in the cartridge, the discharge of the dental viscous material contained in the cartridge can be started as in the jamming mechanism type.

Also, while the dental viscous material contained in the cartridge is surely pressed at a constant stroke, because of the construction of the jamming mechanism type, when the inner pressure increases over a predetermined pressure, the pressure is released, thereby preventing a "afterflow" phenomenon from occurring.

Further, nevertheless various materials including from low-viscosity materials to high-viscosity materials can be applied to the dental viscous material contained in the cartridge, the dental viscous material can be discharged with an accurate measurement from the first discharge.

Moreover, the embodiments as recited in appended claims 2 thru 5 are more preferable.

In the light of the above, the dispenser for dental viscous material according to this invention having various effects greatly contributes to improvements in technology in the dental remedy.

While the invention has been described in detail and with reference to specific embodiments thereof, it will be apparent to one skilled in the art that various changes and modifications can be made therein without departing from the spirit and scope thereof.

What is claimed is:

1. A dispenser for dental viscous material comprising:
   a box-shaped handle at a front end of which is provided a cartridge-mounting portion for mounting a cartridge containing a dental viscous material;
   a guide shaft supported slidably in the front and back direction in a cavity of said box-shaped handle, at a predetermined position of which is provided a lever-engaging portion;
   a lever mounted oscillatorily in said box-shaped handle via a lever shaft, one end of which is engaged with said lever-engaging portion of said guide shaft and the other end of which is positioned outside said box-shaped handle;
   an elastic member engaged with said box-shaped handle and said guide shaft or said lever so as to return said guide shaft to an initial position;
   a slide block having therein a space whose lower side is opened and having a box-like outer shape corresponding to a shape of the cavity of said box-shaped handle and being screwed with an adjusting screw at a position lower than that of a through hole bored in a front side wall member, through which is penetrated said guide shaft in the front and back direction;
   a pressing spring for pressing forward a release plate bored with a hole having a size slightly larger than that of said guide shaft and having a shape corresponding to that of said guide shaft, through which is penetrated said guide shaft, the release plate being able to be mounted so as to be inclined against an axis of said guide shaft by adjusting a backward protruded length of said adjusting screw, and said pressing spring being aligned between a rear side wall member of said slide block and said release plate;
   a piston shaft for pressing said viscous material in said cartridge from said rear side, said piston shaft having an axis in parallel to that of said guide shaft and being fixed to said slide block; and
   a braking member for at all times pressing said piston shaft by an elastic force of a braking elastic member, said braking member being aligned in said box-shaped handle.

2. The dispenser for dental viscous material according to claim 1, wherein said braking member is spherical, and said braking elastic member for at all times pressing said braking member against said piston shaft is a coil spring.

3. The dispenser for dental viscous material according to claim 1, wherein when said elastic member for returning said guide shaft to an initial position is a coil spring whose one end face comes into contact with a front end face of said guide shaft and whose another end face comes into contact with an end face of a set screw to be screwed with a female screw provided in a first half portion of a front mounting hole of said box-shaped handle, the screwing position of said set screw being movable in said front and back direction.

4. A dispenser for dental viscous material as claimed in claim 1, wherein a back lid is fixed in a lower side of said box-shaped handle, and said back lid is provided with a skirt portion, which is deeper than said front side wall member of the slide block protruding from a bottom face of said box-shaped handle and a lower end of said release plate.

5. A dispenser for dental viscous material as claimed claim 1, wherein a stopper having a portion protruding downward is mounted movably in an intermediate portion of said lever.

* * * * *